(12) United States Patent
Thomas et al.

(10) Patent No.: US 9,907,632 B2
(45) Date of Patent: *Mar. 6, 2018

(54) DISPOSABLE DENTAL VALVE DEVICE HAVING A CHECK VALVE

(71) Applicant: STOMA VENTURES, LLC, Chesterfield, MO (US)

(72) Inventors: Charles Thomas, Vero Beach, FL (US); Edward Arguello, Weston, FL (US)

(73) Assignee: STOMA VENTURES, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/619,830

(22) Filed: Jun. 12, 2017

(65) Prior Publication Data

US 2017/0273767 A1  Sep. 28, 2017

Related U.S. Application Data

(63) Continuation of application No. 15/092,264, filed on Apr. 6, 2016, now Pat. No. 9,693,842, and a
(Continued)

(51) Int. Cl.
| | |
|---|---|
| *F16K 15/18* | (2006.01) |
| *F16K 15/14* | (2006.01) |
| *A61C 17/06* | (2006.01) |
| *F16K 5/04* | (2006.01) |
| *A61C 17/16* | (2006.01) |
| *F16K 5/10* | (2006.01) |

(Continued)

(52) U.S. Cl.
CPC ............ *A61C 17/04* (2013.01); *F16K 5/0407* (2013.01); *F16K 15/144* (2013.01); *F16K 15/185* (2013.01); *F16K 15/188* (2013.01); *A61C 1/0061* (2013.01); *A61M 2039/244* (2013.01); *A61M 2205/0205* (2013.01); *F16K 5/10* (2013.01)

(58) Field of Classification Search
CPC ...... F16K 15/144; F16K 15/16; F16K 15/181; F16K 15/185; F16K 15/188; A61C 1/0061; A61C 17/04; A61M 39/24; A61M 2039/226; A61M 2039/244; Y10T 137/86944
USPC ........................................................ 137/630
See application file for complete search history.

(56) References Cited

U.S. PATENT DOCUMENTS 3,348,569 A * 10/1967 Frye ...................... F16K 15/188
                                                                137/269.5
3,363,650 A *  1/1968 Scaramucci .......... F16K 15/188
                                                                137/269.5
(Continued)

*Primary Examiner* — Mary McManmon
*Assistant Examiner* — Richard K Durden
(74) *Attorney, Agent, or Firm* — David H. Chervitz

(57) ABSTRACT

A dental valve device is disclosed having a valve body having a tip receiving end, a hose receiving end, a lumen formed between the tip receiving end and the hose receiving end, a partial opening formed in the valve body and a rotatable valve sealing body adapted to be inserted into the partial opening, the rotatable valve sealing body having a bore for alignment with the lumen formed between the tip receiving end and the hose receiving end, the bore having a tip receiving opening and a hose receiving opening, the rotatable valve sealing body having a check valve positioned in the bore.

17 Claims, 13 Drawing Sheets

Related U.S. Application Data continuation-in-part of application No. 14/925,749, filed on Oct. 28, 2015.

(51) Int. Cl.
*A61C 1/00* (2006.01)
*A61M 39/24* (2006.01)

(56) References Cited

U.S. PATENT DOCUMENTS

| | | | | |
|---|---|---|---|---|
| 3,474,818 A * | 10/1969 | Hartman | ............... | F16K 5/045 |
| | | | | 137/269.5 |
| 3,565,099 A * | 2/1971 | Huber | ............... | F16K 5/0407 |
| | | | | 137/269.5 |
| 3,628,565 A * | 12/1971 | McWethy | ............ | F16K 15/144 |
| | | | | 137/515.5 |
| 4,928,725 A * | 5/1990 | Graves | ................ | F16K 5/0605 |
| | | | | 137/269.5 |
| 4,966,551 A * | 10/1990 | Betush | ................ | A61C 17/043 |
| | | | | 433/126 |
| 4,969,484 A * | 11/1990 | Graves | ................ | F16K 15/181 |
| | | | | 137/269.5 |
| 5,004,005 A * | 4/1991 | Graves | ................ | F16K 5/0605 |
| | | | | 137/269.5 |
| 5,295,830 A * | 3/1994 | Shen | ................... | A61C 1/16 |
| | | | | 433/116 |
| 5,373,868 A * | 12/1994 | Rodriguez | ........... | F16K 5/0605 |
| | | | | 137/543 |
| 5,595,206 A * | 1/1997 | Soria Vega | ........... | F16K 27/067 |
| | | | | 137/15.22 |
| 9,693,842 B2 * | 7/2017 | Thomas | ............... | A61C 17/04 |
| 2003/0014842 A1* | 1/2003 | Niendorf | .............. | A61C 17/043 |
| | | | | 16/430 |
| 2006/0027270 A1* | 2/2006 | Truitt | .................... | A61M 39/02 |
| | | | | 137/843 |
| 2014/0017335 A1* | 1/2014 | Dimov | ................. | C08K 3/005 |
| | | | | 424/618 |
| 2014/0170595 A1* | 6/2014 | Williams | .............. | A61C 17/04 |
| | | | | 433/95 |
| 2014/0239551 A1* | 8/2014 | Williams | .............. | A61C 17/04 |
| | | | | 264/328.13 |
| 2017/0120036 A1* | 5/2017 | Thomas | ............... | A61M 39/24 |
| 2017/0122443 A1* | 5/2017 | Arguello | .............. | F16K 5/0442 |

\* cited by examiner

DISPOSABLE DENTAL VALVE DEVICE HAVING A CHECK VALVE

RELATED APPLICATION

This application is a continuation of U.S. patent application Ser. No. 15/092,264, filed on Apr. 6, 2016, which was a continuation-in-part application of U.S. patent application Ser. No. 14/925,749, filed on Oct. 28, 2015, the disclosures of which is incorporated herein by reference.

BACKGROUND

This disclosure relates to a valve for a dental instrument for removing saliva and other fluids from a mouth of a patient and more particularly to a valve for a dental instrument which incorporates a check valve for preventing backflow of saliva, debris, and other fluids back into the mouth of the patient.

During a dental procedure it is important to be able to remove saliva, blood, water, tooth fragments, metals, and other debris or fluids from the mouth of a patient. Removal of this matter allows a dentist to be able to perform a procedure in an unobstructed manner. Various systems or devices have been developed to remove liquid and solid materials from a mouth during a dental procedure. One device that is capable of removing saliva is known as a saliva ejector or a low volume ejector. A saliva ejector typically comprises a plastic flexible tube for placement in the mouth of a patient. The saliva ejector tube is connected to a valve which in turn is connected via suction tubing to a source of vacuum. In this manner, saliva is passed through the ejector tube, the valve, and the tubing to be disposed of in a sanitary manner. Once the procedure is completed, the ejector should be discarded and the valve should be sterilized by autoclaving to be used again. Although it is suggested to autoclave the valve after each use, it is known that autoclaving is hardly ever done. Another device that is capable of removing solid materials is a high volume evacuator system. A high volume evacuator system generally consists of a tube that may be inserted into a mouth of a patient with the tube connected to a valve which is connected via a tubing to a source of vacuum. Again, in this manner, debris may be removed from the mouth of the patient. After the dental procedure, the tube is disposed of and the valve should be sterilized for reuse. However, although it is suggested to sterilize the valve after use, it is known that this suggested procedure is hardly ever followed.

As can be appreciated, the saliva ejector and the high volume evacuator are used to remove liquids and debris from a mouth of a patient to prevent a patient from swallowing or aspirating liquids and debris produced during a dental procedure. Typically, when using these evacuator devices there is no backflow back into the mouth of a patient. However, there are times when backflow or a reverse flow may take place and previously removed liquids and debris may flow back into the mouth of the patient. It is also possible that if the systems are not properly maintained that fluids and debris from a previous patient may flow back into the mouth of a subsequent patient. These situations may be dangerous, are undesirable, and should be avoided.

In order to prevent backflow, there are various devices that are separate from the saliva ejector. These devices are inserted between the flexible tube and the dental valve or between the dental valve and suction tubing. These devices tend to be complex and expensive. Further, these devices have to be separately purchased, inventoried, and used apart from the flexible tube and the dental valve.

Therefore, it would be desirable to have a valve for a dental instrument that incorporates a check valve for preventing a backflow condition. It would also be desirable to have a disposable dental valve having a check valve that is easy to install on or remove from suction tubing for a source of vacuum. Further, it would be advantageous to have a disposable dental valve having a check valve that is disposable.

BRIEF SUMMARY

In one form of the present disclosure, a dental valve device comprises a valve body having a tip receiving end, a hose receiving end, a lumen formed between the tip receiving end and the hose receiving end, a partial opening formed in the valve body, and a rotatable valve sealing body adapted to be inserted into the partial opening, the rotatable valve sealing body having a bottom having an opening, a bore for alignment with the lumen formed between the tip receiving end and the hose receiving end, the bore having a tip receiving opening and a hose receiving opening, the rotatable valve sealing body having a check valve positioned in the bore and the opening in the bottom.

In another form of the present disclosure, disposable dental valve device comprises a valve body having a tip receiving end, a hose receiving end, a lumen formed between the tip receiving end and the hose receiving end, a partial opening formed in the valve body, a rotatable valve sealing body adapted to be inserted into the partial opening, the rotatable valve sealing body having a bottom having an opening, a bore for alignment with the lumen formed between the tip receiving end and the hose receiving end, the bore having a tip receiving opening and a hose receiving opening, and a check valve positioned in the bore and the opening in the bottom, the check valve having a flap portion and a retention portion with the flap portion positioned in the bore and the retention portion retained against the bottom.

In yet another form of the present disclosure, a disposable dental valve device comprises a valve body having a tip receiving end, a hose receiving end, a lumen formed between the tip receiving end and the hose receiving end, a partial opening formed in the valve body, a rotatable valve sealing body adapted to be inserted into the partial opening, the rotatable valve sealing body having a bottom, a bore for alignment with the lumen formed between the tip receiving end and the hose receiving end, the bore having a tip receiving opening and a hose receiving opening, the bottom having an opening, a first ledge member, a second ledge member having a first ledge portion, a central indented ledge portion, and a second ledge portion, and a check valve positioned in the bore and the opening in the bottom, the check valve having a flap portion and a retention portion with the flap portion positioned in the bore and the retention portion retained against the bottom, the retention portion having a first end, a central portion having an extension member, and a second end with the first end and the second end for being positioned between the first ledge member and the second ledge member and the extension member for fitting into the central indented ledge portion.

The present disclosure provides a disposable dental valve device having a check valve for use with a dental instrument that is suitable for one time use and may be discarded after a single use.

The present disclosure provides a disposable dental valve device having a check valve that is easy to install on suction tubing connected to a source of vacuum and have a tip installed on another end of the disposable dental valve device.

The present disclosure provides a disposable dental valve device having a check valve that is small, lightweight, easy to handle, easy to install, and easy to operate.

The present disclosure also provides a disposable dental valve device having a check valve which is of simple construction and design and which can be easily employed with highly reliable results.

The present disclosure is related to a disposable dental valve device having a check valve that does not require sterilization and prevents against any backflow and cross-contamination.

The present disclosure provides a disposable dental valve device having a check valve that may have an antimicrobial agent or chemical incorporated into the device to prevent any bacterial growth on the device. The antimicrobial agent or chemical may also be a coating applied to the disposable dental valve device having a check valve.

The present disclosure is related to a disposable dental valve device having a check valve that may be constructed of plastic that is recyclable or biodegradable to reduce the cost of the device and to allow the device to be disposable and discarded after a single use.

The present disclosure provides a disposable dental valve device having a check valve that further includes a cap device that may be used to cap off a suction tubing connected to a source of vacuum when the disposable dental valve device having a check valve is removed from the suction tubing connected to the source of vacuum to reduce or eliminate any sound or noise associated with the source of vacuum.

The present disclosure is related to a disposable dental valve device having a check valve that has a valve sealing body that is easy to manipulate during a dental operation to open or close the valve and also incorporates a check valve to automatically prevent backflow of saliva, liquid, or other material.

The present disclosure is also related to a method for manufacturing a disposable dental valve device having a check valve by injection molding.

These and other advantages of the present disclosure will become apparent after considering the following detailed specification in conjunction with the accompanying drawings, wherein:

DETAILED DESCRIPTION OF PREFERRED EMBODIMENTS

Figure 1:
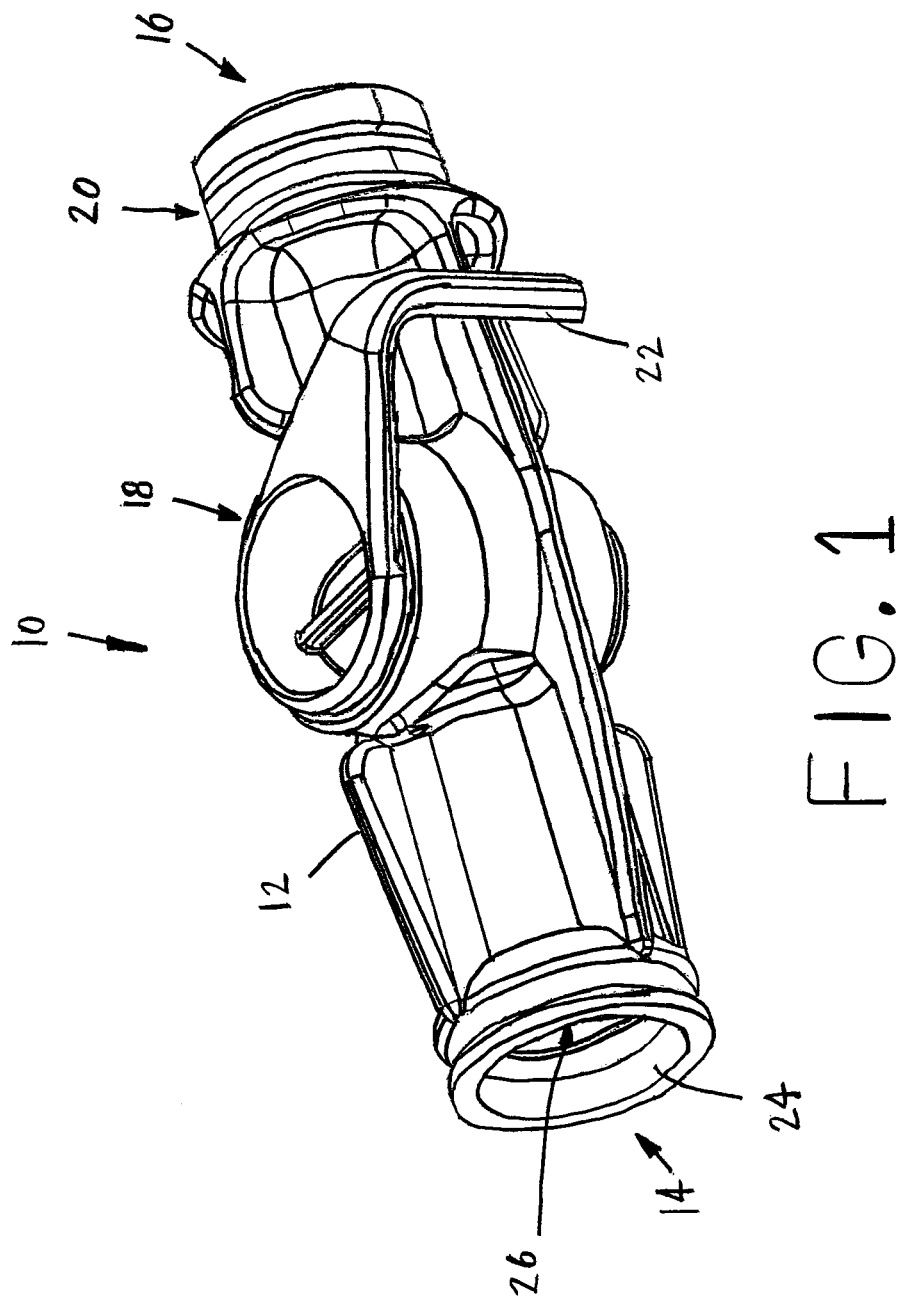
FIG. 1 is a perspective view of a disposable dental valve device having a check valve constructed according to the present disclosure.

Referring now to the drawings, wherein like numbers refer to like items, number 10 identifies a disposable dental valve device for use with a dental system (not shown) constructed according to the present disclosure. With reference now to FIG. 1, the valve 10 comprises a valve body 12 having a tip receiving end 14, a suction tubing or hose receiving end 16, and a rotatable valve sealing body 18. The tip receiving end 14 is adapted to receive an evacuator tip device (not shown) such as a high volume evacuator or a low volume evacuator (saliva ejector). The hose receiving end 16 is adapted to receive a vacuum line or a hose (not shown) which is connected to a suction system (also not shown) which is used to dispose of any saliva, liquid, or debris removed from a mouth of a patient. The hose receiving end 16 also has a circumferential channel 20 that is adapted to accept an O-ring (not shown). The O-ring is used to further secure a hose or a tailpiece to the hose receiving end 16. It is also possible that the hose receiving end 16 may incorporate a structure to secure a hose to the end 16 without the use of the channel 20 or the requirement for an O-ring. For example, the end 16 may be barbed so that the barbs may hold a hose thereon. The device 10 is constructed of material that allows the device 10 to be disposable and suitable for one time use. The device 10 also has a handle 22 for manual operation of the rotatable valve sealing body 18 of the device 10. Manual operation of the handle 22 will open the device 10, close the device 10, or partially open the device 10, as will be discussed more fully herein. As can be appreciated, a suction system provides suction through an evacuator tip device, the device 10, and a hose so that any debris, liquid, or saliva that is introduced into an evacuator tip device is removed through an evacuator tip device, the valve 10, and a hose when the rotatable valve sealing body 18 of the device 10 is in an open state or a partially open state. The valve body 12 also has an opening 24 at the tip receiving end 14 and a passage or lumen 26 formed in the valve body 12. The lumen 26 continues through the valve body 12 to the hose receiving end 16. Although not shown, it is contemplated that the tip receiving end 14 may be constructed having an interior annular ring for receiving an O-ring to retain a tip therein. It is also possible that the tip receiving end 14 may have other structure that will allow a frictional engagement of a tip and the tip receiving end 14.

Figure 2:
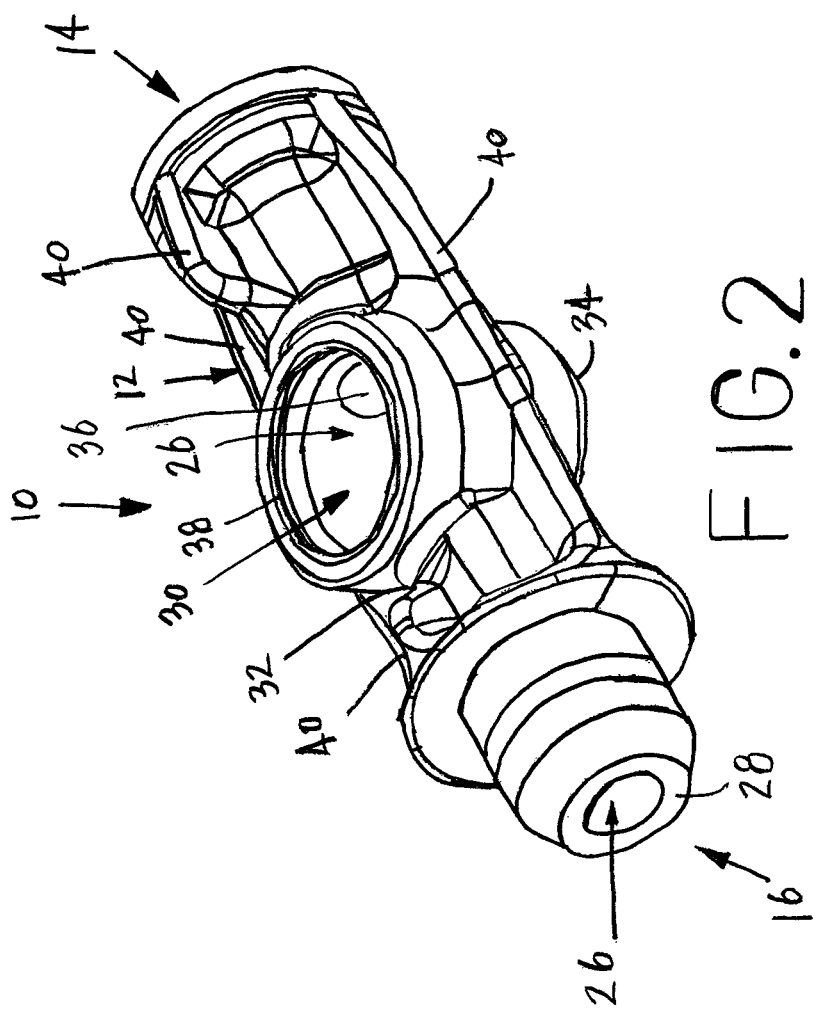
FIG. 2 is a perspective view of a disposable dental valve device having a check valve constructed according to the present disclosure with a valve sealing body removed.

With reference now to FIG. 2, the device 10 is shown with the rotatable valve sealing device 18 being removed. The valve body 12 has the lumen 26 and an opening 28 at the hose receiving end 16. As has been described, the lumen 26 continues through the valve body 12 to the tip receiving end 14. The valve body 12 also has a partial opening 30 formed on a top side 32 of the valve body 12. The partial opening 30 does not go all the way through the valve body 12. The partial opening 30 is blocked by a bottom 34 of the valve body 12. An opening 36 is also shown in the lumen 26 between the tip receiving end 14 and the opening 30. An annular channel or ring 38 is formed in the opening 30 which is used to retain the rotatable valve sealing device 18 in place, as will be explained in further detail herein. The valve body 12 also has exterior ribs 40 that add strength to the valve body 12 and also assist in forming the valve body 12.

Figure 3:
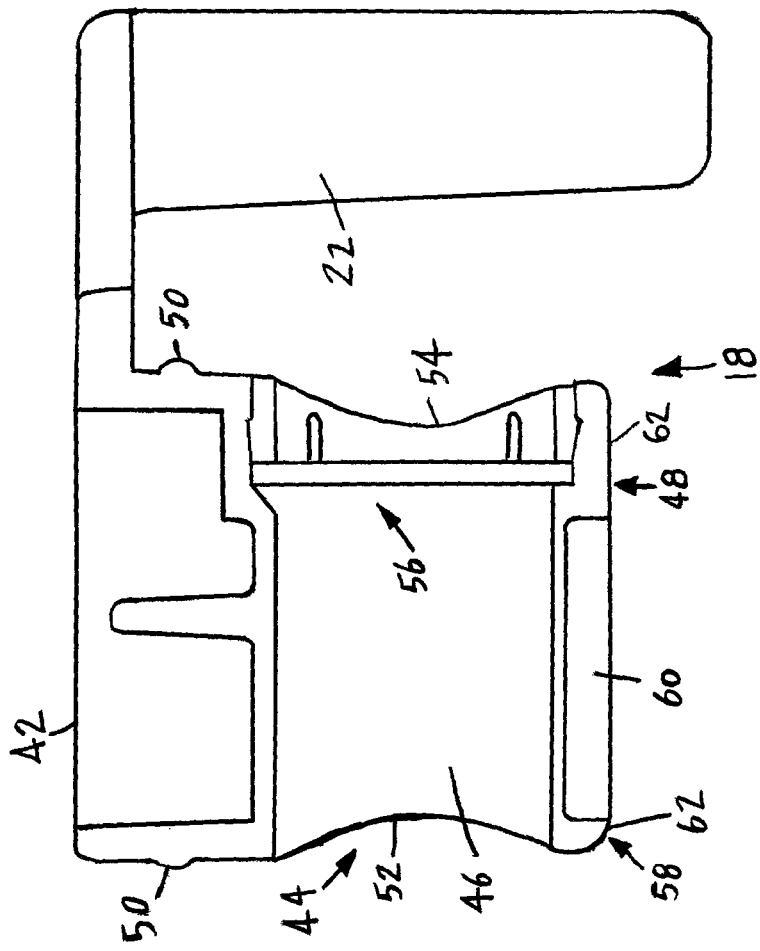
FIG. 3 is a cross-sectional view of a valve sealing body constructed according to the present disclosure with a check valve in a closed position.

FIG. 3 shows a cross-sectional view of the rotatable valve sealing body 18 with the body 18 having been removed from the valve body 12. The rotatable valve sealing body 18 has a top 42, a central body portion 44 having a bore 46, and a bottom 48. The handle 22 is part of the top 42. The central body portion 44 also has an annular ridge portion 50 near the top 42. The ridge portion 50 is capable of fitting into the ring 38 (FIG. 2) in a snap fit engagement to secure the rotatable valve sealing body 18 within the valve body 12. The bore 46 is adapted to be aligned with the lumen 26 of the valve body 12. The bore 46 of the rotatable valve sealing body 18 also has a first opening 52 and a second opening 54. The first opening 52 is used to be aligned with the opening 28 (FIG. 2) in the valve body 12. The second opening 54 is used to be aligned with the opening 36 (FIG. 2) of the valve body 12. The second opening 54 has a check valve 56 positioned therein to selectively open or close the second opening 54. The check valve 56 is provided for allowing liquid, saliva, or debris to pass from the tip receiving end 14, the check valve 56, the bore 46, the first opening 52, and out the hose receiving end 16 when the check valve 56 is opened. However, the check valve 56 also prevents any liquid, saliva, or debris from passing or traveling from the hose receiving end 16, the first opening 52, the bore 46, and through the check valve 56 when the check valve 56 is closed. The check valve 56 will close when a reduced pressure occurs from an interaction of a mouth of a patient on an evacuator tip device. For example, a patient may be requested to close the mouth of the patient around the evacuator tip device. When this occurs, a reduced pressure results in which a backflow may occur. The check valve 56 is sensitive to this pressure differential and will close to prevent backflow. The check valve 56 is shown in the closed position in FIG. 3.

As can be appreciated, when the bore 46 is aligned with the lumen 26, the device 10 is in an open position and the source of vacuum will draw any fluid, saliva, or debris from the tip receiving end 14 through the lumen 26 and the bore 46 and out through the hose receiving end 16. The check valve 56 is in an open position or configuration at this particular time. In this manner, fluid, saliva, and debris may be removed from a mouth of a patient during a dental procedure or operation. Although the ridge 50 is shown, it is possible that an annular ring may be formed in the central body portion 44 and an O-ring may be used to hold the valve sealing body 18 in place. Also, although one ridge 50 is depicted, it is contemplated that another ridge 50 may be formed on the central body portion 44 near the bottom 48 and another ring 38 be formed in the opening 30 near the bottom 34 to receive the second ridge 50 to further secure the valve sealing body 18 in place.

The rotatable valve sealing body 18 also has an annular ring 58 formed in the bottom 48. A central indentation 60 is formed within the annular ring 58. The annular ring 58 has a surface 62 that contacts an interior surface (not shown) of the bottom 34 of the valve body 12. The annular ring 58, the central indentation 60, and the surface 62 facilitate smooth and easy rotation of the rotatable valve sealing body 18 within the valve body 12. The annular ring 58, the central indentation 60, and the surface 62 further allow rotation of the body 18 without being bound up within the valve body 12.

Figure 4:
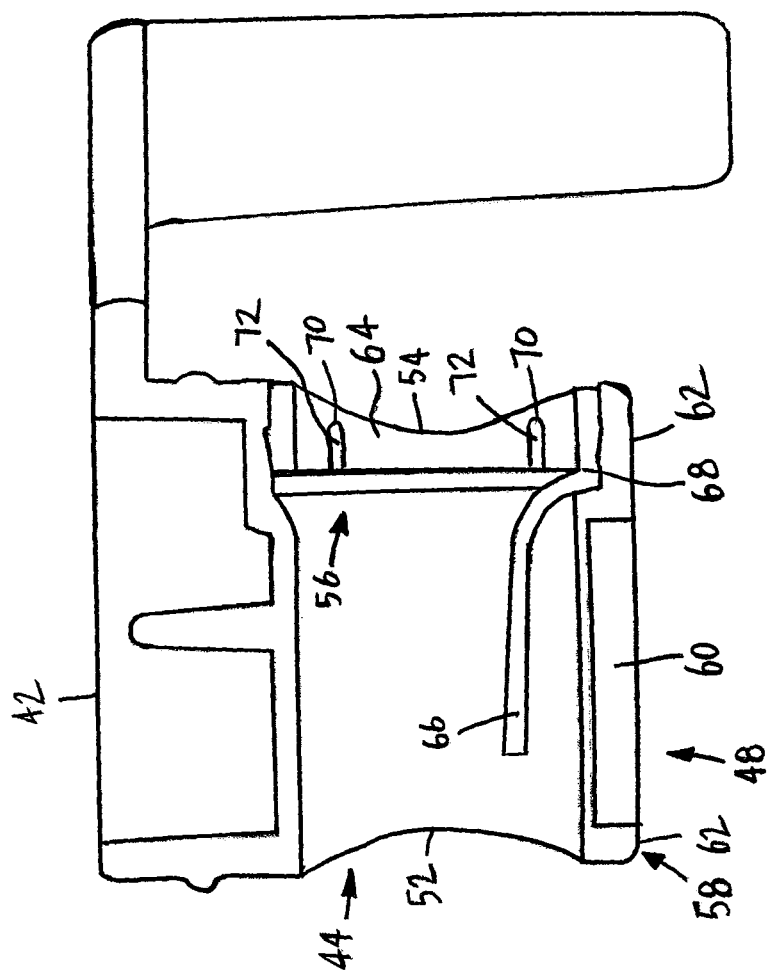
FIG. 4 is a cross-sectional view of the valve sealing body shown in FIG. 3 with a check valve an opened position.

Referring now to FIG. 4, the check valve 56 of the rotatable valve sealing body 18 is illustrated in the open position. The check valve 56 comprises a housing 64 having a flap portion 66 being connected at an end portion 68. The connection of the flap portion 66 at the end portion 68 allows the check valve 56 to open or close. The end portion 68 may be a hinge device that allows the flap portion 66 to move relative to the housing 64. The housing 64 also has retaining rib openings 70 formed in the housing 64. The rotatable valve sealing body 18 has retaining ribs 72 formed in the second opening 54. The openings 70 are used to receive the ribs 72 therein for retaining the check valve 56 in the second opening 54. In this manner, a snap fit engagement of the check valve 56 within the second opening 54 is provided. Although the openings 70 and the ribs 72 are shown, it is possible that other retention or engagement type constructions are contemplated, such as using an adhesive or forming the check valve 56 and the body 18 as a unitary piece or construction. As can be appreciated, when the flap portion 66 is in the open position the flap portion 66 will only be within the bore 46 of the body 18. The rotatable valve sealing body 18 is also shown having the top 42, the central body portion 44 having the first opening 52 and the second opening 54, the bottom 48, the annular ring 58, the central indentation 60, and the surface 62. The openings 52 and 54 are concave and this provides for smooth rotation of the body 18 within the valve body 12.

Figure 5:
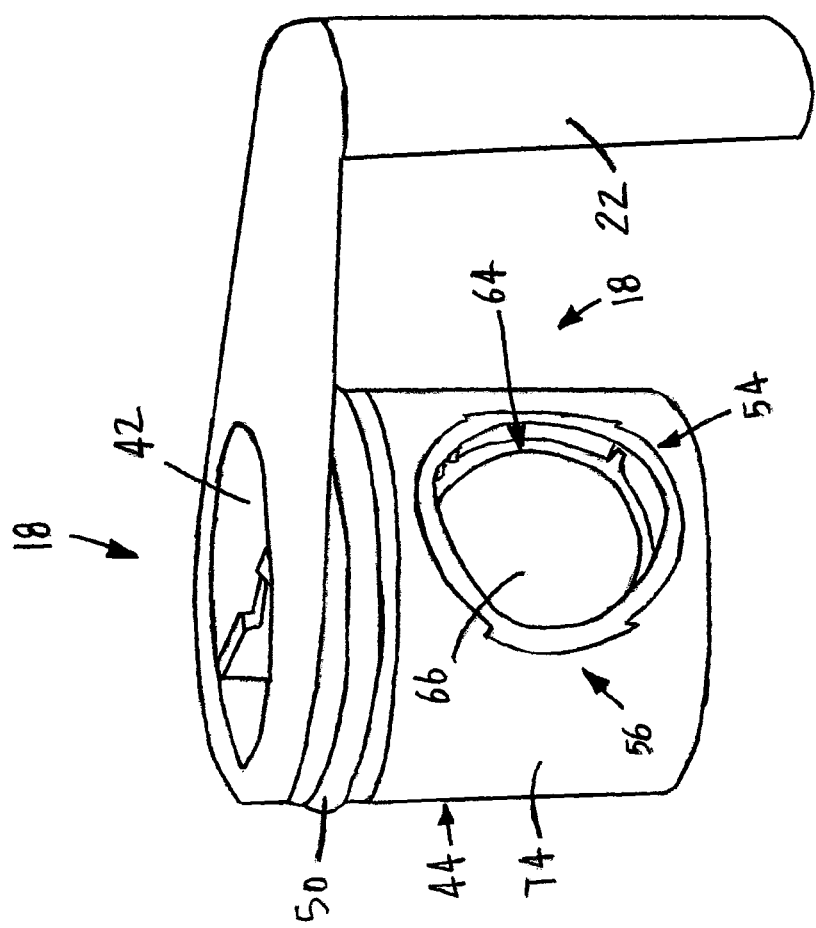
FIG. 5 is a perspective view of the valve seal body constructed according to the present disclosure with the check valve shown in the closed position.

FIG. 5 shows a perspective view of the rotatable valve sealing body 18 with the check valve 56 in the closed position. The housing 64 is positioned in or on the second opening 54. The flap portion 66 is positioned up against the housing 64. With the flap portion 66 in this position, the closed position, no fluid, saliva, or debris will flow through the body 18. The body 18 has the central body portion 44 having an exterior surface 74. The annular ridge portion 50 is positioned near the top 42. Also, the handle 22 is part of the top 42.

Figure 6:
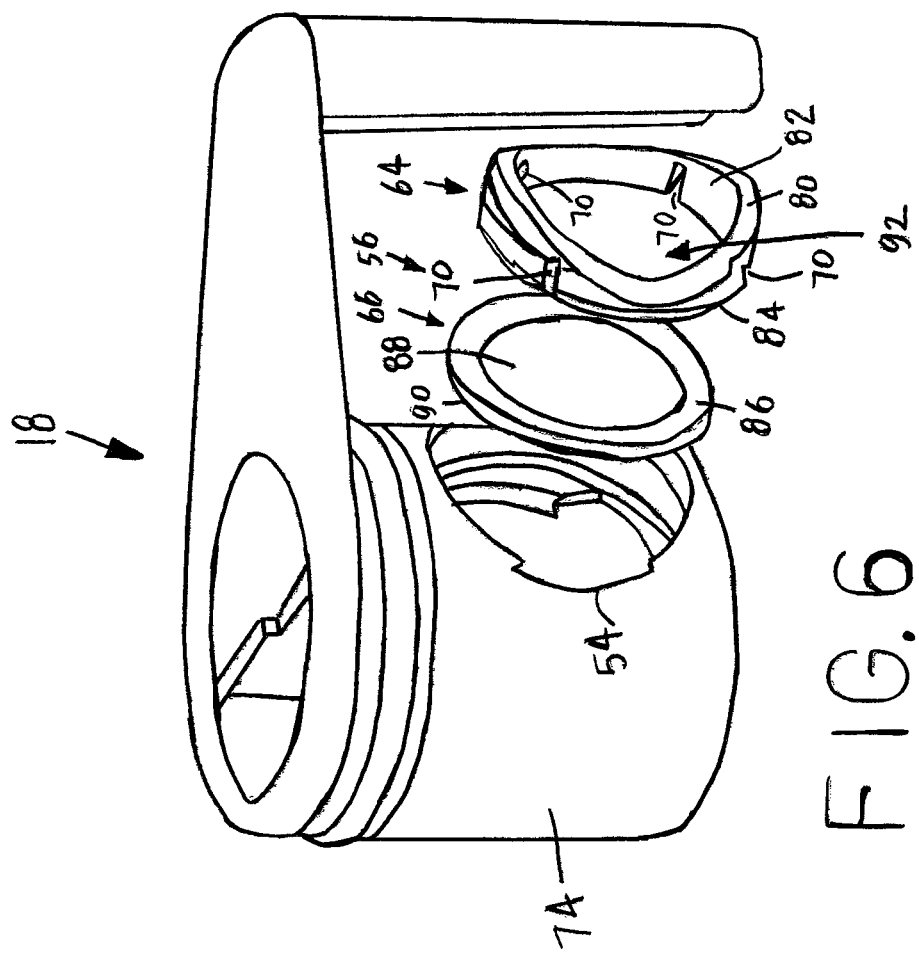
FIG. 6 is a perspective view of the valve seal body constructed according to the present disclosure with the check valve removed from the valve seal body and shown in an exploded view.

With reference now to FIG. 6, a perspective view of the rotatable valve sealing body 18 is shown with the check valve 56 removed from the second opening 54. The check valve 56 is also depicted in an exploded view in that the housing 64 and the flap portion 66 have been separated. As has been discussed, the housing 64 and the flap portion 66 may be a unitary construction. The housing 64 has a front surface 80 that is concave to follow the concave second opening 54 so that the front surface 80 is flush with the exterior surface 74 when the housing 64 is inserted into the second opening, as is depicted in FIG. 5. The housing 64 also has a center portion 82 and a back 84. The center portion 82 and the back 84 have the openings 70 formed therein. Although four openings 70 are shown, it is contemplated that more or less openings 70 may be provided in the housing 64. The flap portion 66 has a front side 86, a center portion 88, and a back side 90. The front side 86 and the center portion 88 are sized and shaped to fit over the center portion 82 and the back 84 of the housing 64. As can be appreciated, the flap portion 66 is a solid piece and the housing 64 has a central opening 92. The flap portion 66 is used to cover or close the central opening 92. It is also possible that the back 84 may have a recess, groove, or rabbet formed therein to receive or seat the flap portion 66 therein. The flap portion 66 may be connected to the housing 64 in any suitable manner. The second opening 54 has the ribs 72 that are used to capture the openings 70 to hold the housing 54 in place in or around the second opening 54. Although four ribs 72 are depicted, as with the openings 70, more or less ribs 72 are possible.

Figure 7:
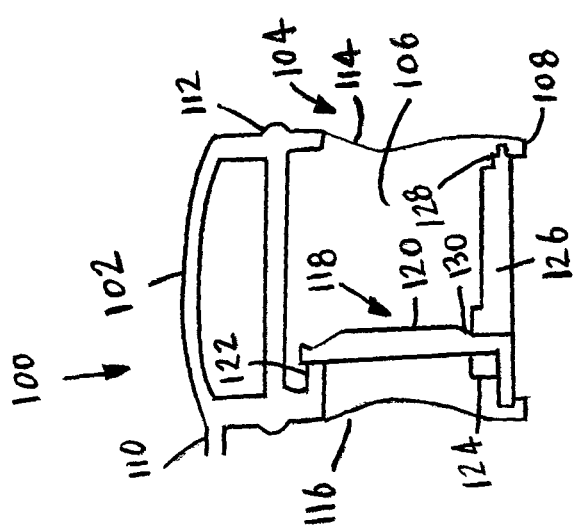
FIG. 7 is a partial cross-sectional view of another embodiment of a valve sealing device having a check valve shown in a closed position constructed according to the present disclosure.
Figure 8:
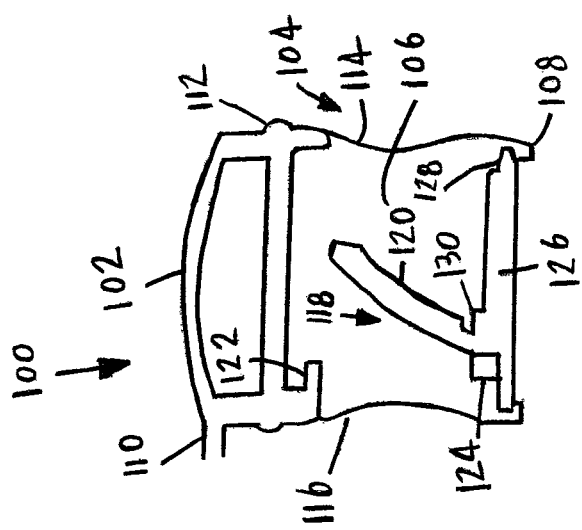
FIG. 8 is a partial cross-sectional view of another embodiment of a valve sealing device having a check valve shown in a partially open position constructed according to the present disclosure.

FIGS. 7 and 8 illustrate another embodiment of a rotatable valve sealing body 100 constructed according to the present disclosure. The rotatable valve sealing body 100 is shown in cross-section in both FIGS. 7 and 8. Also, the rotatable valve sealing body 100 may replace the rotatable valve sealing body 18 and be inserted into the body 12. The rotatable valve sealing body 100 comprises a top 102, a central body portion 104 having a bore 106, and a bottom 108. A portion of handle 110 is shown which is part of the top 102. The central body portion 104 also has an annular ridge portion 112 near the top 102. The bore 106 is adapted to be aligned with the lumen 26 of the valve body 12. The bore 106 of the rotatable valve sealing body 100 also has a first opening 114 and a second opening 116. The first opening 114 is used to be aligned with the opening 28 (FIG. 2) in the valve body 12. The second opening 116 is used to be aligned with the opening 36 (FIG. 2) of the valve body 12. The second opening 116 has a check valve 118 positioned therein to selectively open or close the second opening 116. The check valve 118 is provided for allowing liquid, saliva, or debris to pass from the tip receiving end 14, the check valve 118, the bore 106, the first opening 114, and out the hose receiving end 16 when the check valve 118 is opened. However, the check valve 118 also prevents any liquid, saliva, or debris from passing or traveling from the hose receiving end 16, the first opening 114, the bore 106, and through the check valve 118 when the check valve 118 is closed. The check valve 118 will close when a reduced pressure occurs from an interaction of a mouth of a patient on an evacuator tip device. As has been indicated, a patient may be requested to close the mouth of the patient around the evacuator tip device. When this occurs, a reduced pressure results in which a backflow may occur. The check valve 118 is sensitive to this pressure differential and will close to prevent backflow.

The check valve 118 has a flap portion 120 that seals against a top seat portion 122 and a bottom seat portion 124 that are formed in the body 100. The flap portion 120 is connected to a bottom plate member 126. The bottom plate member 126 snaps into an opening 128 formed in the bottom 108 of the body 100. The flap portion 120 may be connected to the bottom seat portion 124 by use of a hinge 130 or by any other suitable connection means. When manufacturing the body 100, the flap portion 120 is inserted into the opening 128 and then the bottom plate member 126 is snapped into place in the opening 128 in the bottom 108.

Figure 9:
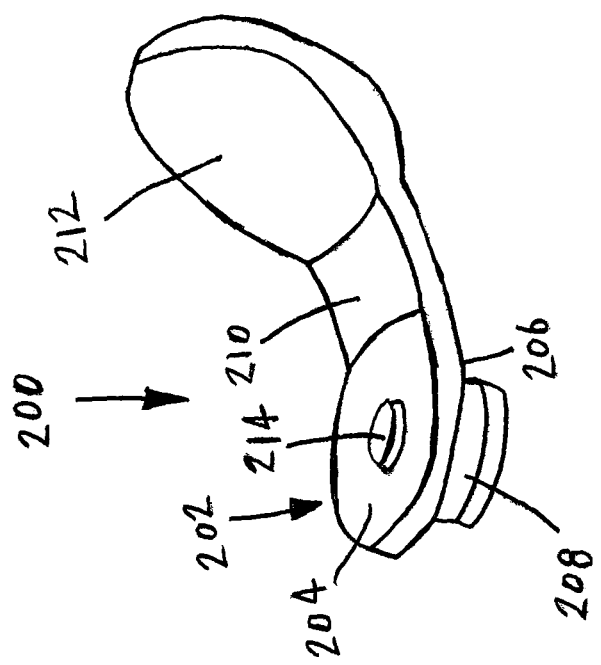
FIG. 9 is a front perspective view of cap device constructed according to the present disclosure.

Referring now in particular to FIG. 9, a cap device 200 is depicted which is used to be placed over the opening of a suction tubing or hose (not shown) when the device 10 is removed from the hose to remove or dispose the device 10. In this manner, the opening of the hose will be physically blocked to shut off any air from rushing into the hose to silence any noise produced by the suction system or a source of vacuum. The cap device 200 is sized and shaped to fit over the opening of the hose. The cap device 200 may be constructed of any suitable material such as rubber or plastic. The valve device 10 may include the cap device 200 so that when the valve device 10 is being removed from the hose for disposal after use the cap device 200 may be placed over the opening of the hose. The cap device 200 comprises a body portion 202 having a top side 204 and a bottom side 206 with the bottom side 206 having a plug portion 208. A central portion 210 is connected between the body portion 202 and a pull 212. The top side 204 has a raised portion or bump 214. The plug portion 208 is inserted into the opening of the hose or flexible tubing connected to a suction source. The pull 212 is used to be grasped by a hand to remove the plug portion 208 and the cap device 200 from the hose when a new disposable dental valve device 10 is to be used. The plug portion 208 may be of a sufficient size and shape to plug an opening associated with a hose attached to a source of suction. The cap device 200 may also be provided separately from the device 10. It is also possible that the cap device 200 may be provided as a kit with the device 10.

Although not shown, it is also possible that the tip receiving end 14 may include an inlet end gasket, such as a balloon gasket, or an O-ring for holding or securing an evacuator tip in place. The inlet end gasket may fit within channels or grooves formed in the tip receiving end 14. It is also possible that the hose receiving end 16 may incorporate a hose adapter or a tailpiece for securing a flexible hose connected to a suction system.

In operation of for example the device 10, with either the body 18 or the body 100 as part of the device 10, the hose receiving end 16 of the device 10 is placed on to a hose connected to a suction system and an evacuator tip is inserted into the tip receiving end 14 and then placed in a mouth of a dental patient. The handle 22, which may include an indicator to indicate the closed position and the open position, is manually operated to open the device 10. Once in the open position, air is allowed to flow through the tip, the tip receiving end 14, the check valve 56, the lumen 26, the bore 46 of the rotatable valve sealing body 18, the hose receiving end 16 and into a suction system. In the event that reduced pressure occurs from an interaction of a mouth of a patient on an evacuator tip device, the check valve 56 will close and no backflow will be allowed from the suction system or the valve device 10. When suction is not needed during a dental procedure, the handle 22 is moved to the closed position. Further, once a dental procedure has been completed, the handle 22 is moved to the closed position, the device 10 is easily separated from the hose, and the cap device 200 is placed over the opening associated with the hose. The cap device 200 will block any air from being sucked into the hose and this silences any noise that is generated by the source of vacuum or the suction system. Once the device 10 is disconnected from the hose, the device 10, which includes the check valve 56 or the check valve 118, may be disposed of by any suitable manner. A new device 10 is then connected to the hose after the cap device 200 is removed. With the new valve device 10 installed, another dental procedure may be initiated.

The disposable dental valve device 10 may be formed of any suitable material such as plastic, polyethylene, and high density polyethylene or any other suitable material that is disposable and recyclable. Any suitable plastic may be used to construct the device 10 so that the device 10 may withstand use in a dental operation or procedure. It is also possible and contemplated to incorporate an antimicrobial agent or chemical in the plastic or to provide a coating of an antimicrobial agent on the plastic to further prevent cross-contamination when using the device 10. As can be appreciated, the antimicrobial agent may be incorporated into any of the components of the device 10.

Figure 10:
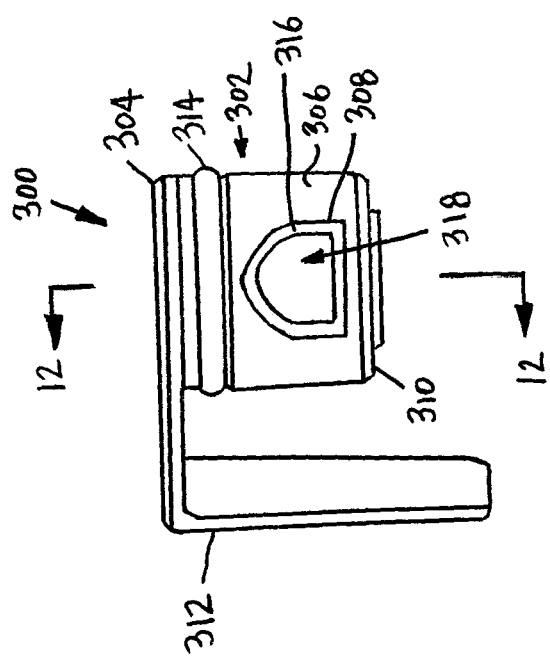
FIG. 10 is a perspective view of another embodiment of a rotatable valve sealing device having a check valve with the check valve shown in a closed position.

FIG. 10 is a perspective view of another embodiment of a rotatable valve sealing device having a check valve 300. The device 300 is capable of being inserted into the valve body 12 (FIG. 2). The device 300 has a rotatable valve sealing body 302 having a top 304, a central body portion 306 having a bore 308, and a bottom 310. A handle 312 is attached to or part of the top 304. The central body portion 306 also has an annular ridge portion 314 near the top 304. The ridge portion 314 is capable of fitting into the ring 38 (FIG. 2) in a snap fit engagement to secure the device 300 within the valve body 12. The bore 308 is adapted to be aligned with the lumen 26 of the valve body 12. The bore 308 of the device 300 also has a first opening 316 that is used to be aligned with the tip receiving end 14 (FIG. 2) in the valve body 12. In the bore 308 is a check valve 318 positioned therein to selectively open or close the bore 308. The check valve 318 is provided for allowing liquid, saliva, or debris to pass from the tip receiving end 14, the bore 308, the check valve 318, and out the hose receiving end 16 (FIG. 2) when the check valve 318 is opened. However, the check valve 318 also prevents any liquid, saliva, or debris from passing or traveling from the hose receiving end 16, the bore 308, and through the check valve 318 when the check valve 318 is closed. The check valve 318 will close when a reduced pressure occurs from an interaction of a mouth of a patient on an evacuator tip device. For example, a patient may be requested to close the mouth of the patient around the evacuator tip device. When this occurs, a reduced pressure results in which a backflow may occur. The check valve 318 is sensitive to this pressure differential and will close to prevent backflow. The check valve 318 is shown in the closed position in FIG. 10.

Figure 11:
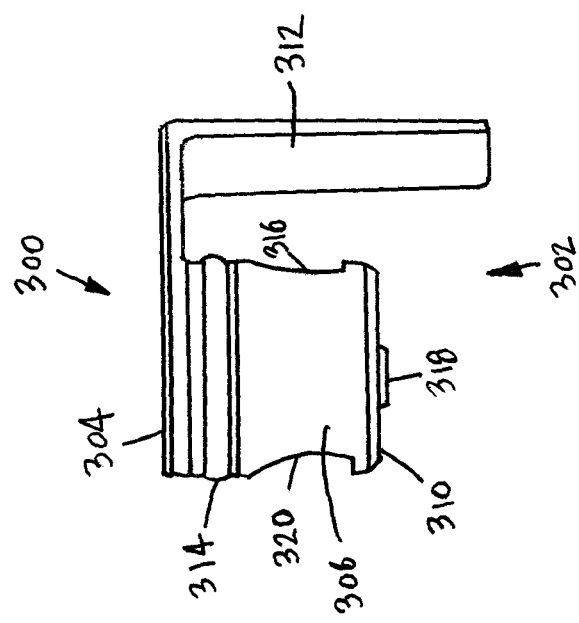
FIG. 11 is a side perspective view of the rotatable valve sealing device shown in FIG. 10.

FIG. 11 illustrates a side perspective view of the rotatable valve sealing device 300. The device 300 has a second opening 320 that is used to be aligned with the opening 28 (FIG. 2) of the hose receiving end 16 in the valve body 12. The device 300 is also shown to have the rotatable valve sealing body 302 having the top 304, the central body portion 306, and the bottom 310. The handle 312 is attached to or part of the top 304. The central body portion 306 also has the annular ridge portion 314 near the top 304. The first opening 316 is also shown. The check valve 318 is further shown extending out of the bottom 310 of the device 300, as will be explained in detail further herein.

Figure 12:
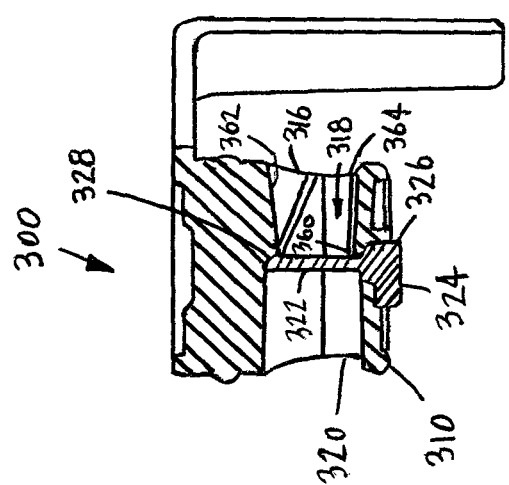
FIG. 12 is a cross-sectional view of the rotatable valve sealing device shown in FIG. 10 taken along the plane of line 12-12.

FIG. 12 depicts a cross-sectional view of the rotatable valve sealing device shown in FIG. 10 taken along the plane of line 12-12. The device 300 has the bore 308 that extends through the central body portion 306 between the first opening 316 and the second opening 320. The check valve 318 comprises a flap portion 322 and a retention portion 324. The check valve 318 is inserted into the bore 308 through an opening 326 formed in the bottom 310. As can be appreciated, the check valve 318 is located within the bore 308 and offset from the first opening 316. The retention portion 324 is retained against the bottom 310. The bore 308 has an upper seat or stop portion 328 against which the flap portion 322 may be positioned when in the closed position. The upper stop portion 328 prevents the flap portion 322 from moving past a vertical position or toward the first opening 316. In this manner, when a reduced pressure occurs from an interaction of a mouth of a patient on an evacuator tip device the flap portion 322 of the check valve 318 will press against the upper stop portion 328 and prevent a backflow condition from occurring. The flap portion 322 prevents any liquid, blood, saliva, or debris present in the suction system, the hose, or the bore 308 from flowing into a mouth of a patient. The bore 308 may also be comprised having a lower seat or stop portion 360 against which the flap portion 322 may be positioned when in the closed orientation. The bore 308 has an upper slanted surface 362 that slants downwardly from the first opening 316 toward the upper stop portion 328. The bore 308 also has a lower slanted surface 364 that slants upwardly from the first opening 316 toward the lower stop portion 360. Also, the first opening 316 may be smaller in diameter than the second opening 320.

Figure 13:
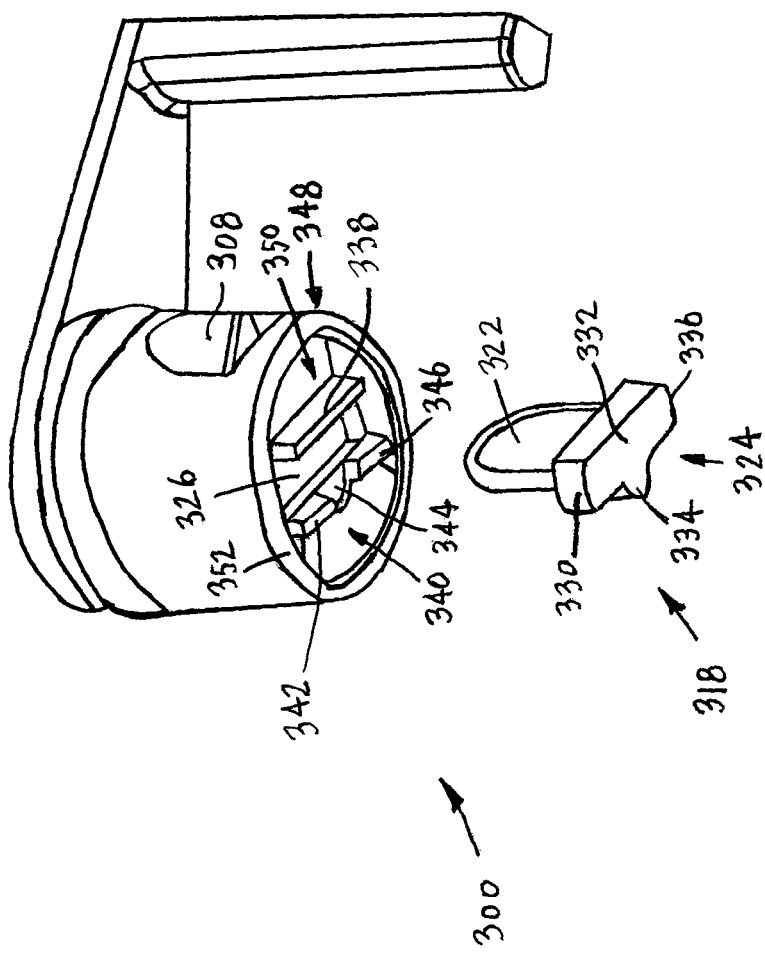
FIG. 13 is an exploded view of the rotatable valve sealing device.

With reference now to FIG. 13, an exploded view of the rotatable valve sealing device 300 is shown. In this particular view, the check valve 318 has been removed from the bore 308 and the opening 326 formed in the bottom 310. The check valve 318 has the flap portion 322 and the retention portion 324. The flap portion 322 is generally semicircular in shape. The retention portion 324 has a first end 330, a central portion 332 having an extension member 334, and a second end 336. The bottom 310 of the device 300 has the opening 326, a first ledge member 338, and a second ledge member 340 having a first ledge portion 342, a central indented ledge portion 344, and a second ledge portion 346. The central indented ledge portion 344 is for capturing the central portion 332 to retain the retention portion 324 in the bottom 310 of the device 300. The first ledge member 338 and the second ledge member 340 are also used to hold the retention portion 324 in place on the bottom 310 of the device 300. The flap portion 322 is sized and shaped to fit through the opening 326 to slide the flap portion 322 in place within the bore 308. The bottom 310 has an annular ring 348 formed in the bottom 310. A central indentation 350 is formed within the annular ring 348. The annular ring 348 has a surface 352 that contacts an interior surface (not shown) of the bottom 34 of the valve body 12. The annular ring 348, the central indentation 350, and the surface 352 facilitate smooth and easy rotation of the rotatable valve sealing body 302 within the valve body 12. The annular ring 348, the central indentation 350, and the surface 352 further allow rotation of the body 302 without being bound up within the valve body 12. The surface 352 may also be eased or chamfered.

The disposable dental valve device 300 may be formed of any suitable material such as plastic, polyethylene, and high density polyethylene or any other suitable material that is disposable and recyclable. It is also possible that the device 300 may be constructed of a material that will allow the device 300 to be reused after the device 300 is cleaned or sanitized. Any suitable plastic may be used to construct the device 300 so that the device 300 may withstand use in a dental operation or procedure. It is also possible and contemplated to incorporate an antimicrobial agent or chemical in the plastic or to provide a coating of an antimicrobial agent on the plastic to further prevent cross-contamination when using the device 300. As can be appreciated, the antimicrobial agent may be incorporated into any of the components of the device 300.

From all that has been said, it will be clear that there has thus been shown and described herein a disposable dental valve device having a check valve which fulfills the various advantages sought therefore. It will become apparent to those skilled in the art, however, that many changes, modifications, variations, and other uses and applications of the subject disposable dental valve device having a check valve are possible and contemplated. All changes, modifications, variations, and other uses and applications which do not depart from the spirit and scope of the disclosure are deemed to be covered by the disclosure, which is limited only by the claims which follow.

What is claimed is:

1. A dental valve device comprises:
   a valve body having a tip receiving end, a hose receiving end, a lumen formed between the tip receiving end and the hose receiving end, a partial opening formed in the valve body; and
   a rotatable valve sealing body adapted to be inserted into the partial opening, the rotatable valve sealing body having a top, a bottom, and a bore for alignment with the lumen formed between the tip receiving end and the hose receiving end, the bore having a tip receiving opening having a top seat portion and a bottom seat portion and a hose receiving opening, a flap portion directly connected to the bottom seat portion by a hinge the rotatable valve sealing body having a bottom opening formed in the bottom, and a bottom plate member for insertion into the bottom opening.

2. The dental valve device of claim 1 wherein the flap portion is movable between an opened position and a closed position.

3. The dental valve device of claim 1 wherein the flap portion seals against the top seat portion when the flap portion is in the closed position.

4. The dental valve device of claim 1 wherein the flap portion moves away from the top seat portion when the flap portion is in the opened position.

5. The dental valve device of claim 1 wherein the rotatable valve sealing body further comprises a handle portion connected to the top.

6. The dental valve device of claim 1 wherein the rotatable valve sealing body, the valve body, the bottom plate member, and the flap portion are constructed of plastic.

7. A disposable dental valve device comprises:
   a valve body having a tip receiving end, a hose receiving end, a lumen formed between the tip receiving end and the hose receiving end, a partial opening formed in the valve body;
   a rotatable valve sealing body adapted to be inserted into the partial opening, the rotatable valve sealing body having a bottom and an opening formed in the bottom and a bore for alignment with the lumen formed between the tip receiving end and the hose receiving end, the bore having a tip receiving opening having a top seat portion and a bottom seat portion and a hose receiving opening;
   a flap portion directly connected to the bottom seat portion by a hinge with the flap portion positioned within the bore adjacent to the tip receiving opening for covering or uncovering the tip receiving opening; and
   a bottom plate member for insertion into the bottom opening.

8. The disposable dental valve device of claim 7 wherein the flap portion seals against the top seat portion when the flap portion is covering the tip receiving opening.

9. The disposable dental valve device of claim 7 wherein the rotatable valve sealing body, the valve body, the flap portion, and the bottom plate member are constructed of plastic.

10. The disposable dental valve device of claim 7 wherein the flap portion moves away from the top seat portion when the flap portion is uncovering the tip receiving end.

11. The disposable dental valve device of claim 7 wherein an antimicrobial agent is incorporated into the flap portion.

12. The disposable dental valve device of claim 7 wherein the rotatable valve sealing body further comprises an annular ridge portion.

13. A disposable dental valve device comprising:
   a valve body having a tip receiving end, a hose receiving end, a lumen formed between the tip receiving end and the hose receiving end, a partial opening formed in the valve body;
   a rotatable valve sealing body adapted to be inserted into the partial opening, the rotatable valve sealing body having a bottom having an opening, a bore for alignment with the lumen formed between the tip receiving end and the hose receiving end, the bore having a tip receiving opening and a hose receiving opening, the tip receiving opening for alignment with the tip receiving end and the hose receiving opening for alignment with the hose receiving end, and a top seat portion and a bottom seat portion formed in the bore adjacent to the tip receiving opening;
   a flap portion directly connected to the bottom seat portion by a hinge with the flap portion positioned within the bore adjacent to the tip receiving opening for covering or uncovering the tip receiving opening, the flap portion forming a check valve; and
   a bottom plate member for insertion into the bottom opening.

14. The disposable dental valve device of claim 13 wherein the flap portion seals against the top seat portion when the flap portion is covering the tip receiving opening.

15. The disposable dental valve device of claim 13 wherein the flap portion moves away from the top seat portion when the flap portion is uncovering the tip receiving end.

16. The disposable dental valve device of claim 13 wherein the rotatable valve sealing body, the valve body, the flap portion, and the bottom plate member are constructed of plastic.

17. The disposable dental valve device of claim 13 further comprising an antimicrobial agent incorporated into the flap portion.

* * * * *